United States Patent
Peng et al.

(10) Patent No.: US 8,599,999 B2
(45) Date of Patent: Dec. 3, 2013

(54) DETECTION SYSTEM, DR IMAGING APPARATUS AND CT IMAGING APPARATUS

(75) Inventors: Hua Peng, Beijing (CN); Jinyu Zhang, Beijing (CN); Quanwei Song, Beijing (CN)

(73) Assignee: Nuctech Company Limited, Beijing (CN)

( * ) Notice: Subject to any disclaimer, the term of this patent is extended or adjusted under 35 U.S.C. 154(b) by 545 days.

(21) Appl. No.: 12/745,978

(22) PCT Filed: Dec. 30, 2009

(86) PCT No.: PCT/CN2009/076264
§ 371 (c)(1),
(2), (4) Date: Jun. 3, 2010

(87) PCT Pub. No.: WO2011/000198
PCT Pub. Date: Jan. 6, 2011

(65) Prior Publication Data
US 2011/0122989 A1    May 26, 2011

(30) Foreign Application Priority Data
Jun. 30, 2009 (CN) .......................... 2009 1 0088630

(51) Int. Cl.
*G03G 15/05* (2006.01)
*G06K 9/00* (2006.01)
*H05G 1/60* (2006.01)

(52) U.S. Cl.
USPC .................................. 378/28; 378/4; 382/103

(58) Field of Classification Search
USPC ............................ 378/4, 28, 62, 57; 382/103
See application file for complete search history.

(56) References Cited

U.S. PATENT DOCUMENTS 5,182,764 A * 1/1993 Peschmann et al. ............ 378/57
5,864,600 A   1/1999 Gray et al.
(Continued)

FOREIGN PATENT DOCUMENTS

CN    1217185      8/2005
CN    101403710    4/2009

OTHER PUBLICATIONS

International Search Report for PCT/CN2009/076264 filed Dec. 30, 2009.

(Continued)

*Primary Examiner* — Irakli Kiknadze
(74) *Attorney, Agent, or Firm* — Westman, Champlin & Koehler, P.A.

(57) ABSTRACT

Disclosed is detection system for detection an object being conveyed along a convey path, the detection system comprises a DR imaging apparatus and a CT imaging apparatus which is provided at the downstream or upstream of the DR imaging apparatus along the convey path, wherein an average speed at which the object passes the DR imaging apparatus is higher than an average speed at which the object passes the CT imaging apparatus. The present invention also relates to a DR imaging apparatus for forming an image of an object by scanning the object, the object being conveyed along a convey path, the DR imaging apparatus comprising: an X-ray source; a detector for detecting passing of the object; a digital image processing unit; and a DR trigger module for data acquisition, wherein during the object passes the DR imaging apparatus, the DR trigger module triggers the DR imaging apparatus to perform data acquisition every time the object passes the DR imaging apparatus a predetermined distance A along the convey path.

19 Claims, 2 Drawing Sheets

(56) References Cited

U.S. PATENT DOCUMENTS

| | | | |
|---|---|---|---|
| 6,078,642 A | 6/2000 | Simanovsky et al. | 378/57 |
| 7,272,510 B2 | 9/2007 | Hansen | |
| 7,325,625 B1 * | 2/2008 | Winters | 173/90 |
| 2006/0182218 A1 * | 8/2006 | An | 378/57 |

OTHER PUBLICATIONS

Office Action from corresponding Chinese Application No. CN200910088630.8, dated Jul. 13, 2011, 4 pgs.

European Search Report and European Search Opinion for European Application No. 09846726.9, dated Feb. 4, 2013, 7 pages.

* cited by examiner

DETECTION SYSTEM, DR IMAGING APPARATUS AND CT IMAGING APPARATUS

CROSS-REFERENCE TO RELATED APPLICATION

This application is a Section 371 National Stage Application of International Application No. PCT/CN2009/076264, filed Dec. 30, 2009, the contents of which are hereby incorporated by reference in their entirety.

FIELD OF INVENTION

The present invention relates to an inspection system which comprises a CT (Computed Tomography) imaging apparatus and a DR (Digital Radiography) imaging apparatus. The present invention also relates to a DR imaging apparatus and a CT imaging apparatus.

BACKGROUND OF INVENTION

Among numerous Explosive-Detection Systems, the CT technology has become prevailing in the aviation security field due to its low false alarm rate and low failed reporting rate. However, the Explosive-Detection System using the CT technology is bulky and costly, which limits the further application.

Though an improved CT Explosive-Detection System having a small volume and a lower cost has been developed recently, the speed at which the object to be inspected passes therethrough is reduced a lot compared to the conventional CT Explosive-Detection System, which also bottlenecks the promoting of it.

In addition, an Explosive-Detection System including a DR imaging apparatus and a CT imaging apparatus is available in the market. The DR imaging apparatus usually obtains data of an object to be inspected in a time triggered mode, specifically, the DR imaging apparatus emits beams at a regular time interval, and detectors receive the beams penetrating the object and convert received information into digital information. This kind of time triggered mode requires a uniform speed of the DR imaging apparatus relative to the object.

However, the adding of the DR imaging apparatus increases the length of the Explosive-Detection System; in addition, the inspecting speed of the CT imaging apparatus is lower than that of the DR imaging apparatus, therefore, the speed at which the object passes the Explosive-Detection System is decreased. In order to obtain the Explosive-Detection System having a small overall dimension, the length added by the DR imaging apparatus has to be as small as possible, thus, the distance between the CT imaging apparatus and the DR imaging apparatus is designed to be small enough.

Further, if the whole length of the object is longer than a distance between a beam plane of the CT imaging apparatus and a beam plane of the DR imaging apparatus, there is the case that the object is scanned by the DR imaging apparatus and the CT imaging apparatus at the same time. In view of the above, the speed at which the object passes the DR imaging apparatus is the same as the speed at which the object passes the CT imaging apparatus in the prior art.

However, the problem is that the imaging time of the DR imaging apparatus is much less than that of the CT imaging apparatus, which means the whole Explosive Detection System has to be operated at a lower speed suitable for the CT imaging apparatus. Thus, if the Explosive Detection System operates at a high speed when the object is scanned by the DR imaging apparatus and operates at a low speed when the object is scanned by the CT imaging apparatus, the average speed at which the objects passes the Explosive Detection System will be increased. In that case, however, the same object is scanned by the DR imaging apparatus at different speeds, which results in distortion of the formed image (as shown in FIG. 2) if no measures are taken, and thus the technical performance of the Explosive Detection System will be deteriorated.

SUMMARY OF INVENTION

In view of the above, the present invention is made to solve or alleviate at least one of the disadvantages or technical problems in the prior art.

According to an aspect of the present invention, there is provided an inspection system for inspecting an object being conveyed along a convey path, the inspection system comprises a DR imaging apparatus and a CT imaging apparatus which is provided at the downstream or upstream of the DR imaging apparatus along the convey path, wherein an average speed at which the object passes the DR imaging apparatus is higher than an average speed at which the object passes the CT imaging apparatus.

The DR imaging apparatus comprises a DR trigger module for data acquisition, and during the object passes the DR imaging apparatus, the DR trigger module triggers the DR imaging apparatus to perform data acquisition every time the object passes the DR imaging apparatus a predetermined distance A along the convey path.

Further, the DR trigger module comprises a rotary encoder provided on the convey path, the rotary encoder outputs a trigger signal to trigger the DR imaging apparatus to perform data acquisition every time it rotates one angle, wherein every time the rotary encoder rotates one predetermined angle, the object passes the predetermined distance A along the convey path. Alternatively, the DR trigger module comprises a plurality of position marks arranged apart at the predetermined distance A along the convey path, and a mark detector for detecting the passing of the position marks, wherein every time the mark detector detects the passing of one of the position marks, the mark detector outputs a trigger signal to trigger the DR imaging apparatus to perform data acquisition.

According to another aspect of the present invention, there is provided an inspection system comprising: a convey path for conveying an object to be inspected; and a DR imaging apparatus arranged along the convey path, wherein the DR imaging apparatus comprises a DR trigger module for data acquisition, and during the object passes the DR imaging apparatus, the DR trigger module triggers the DR imaging apparatus to perform data acquisition every time the object passes the DR imaging apparatus a predetermined distance A along the convey path.

According to further another aspect of the present invention there is provided a DR imaging apparatus for forming an image of an object to be inspected by scanning the object, the object being conveyed along a convey path, the DR imaging apparatus comprises: an X-ray source; a detector for detecting passing of the object; a digital image processing unit; and a DR trigger module for data acquisition, wherein during the object passes the DR imaging apparatus, the DR trigger module triggers the DR imaging apparatus to perform data acquisition every time the object passes the DR imaging apparatus a predetermined distance A along the convey path.

According to still another aspect of the present invention, there is provided a CT imaging apparatus for forming an image of an object to be inspected by scanning the object, the object being conveyed along a convey path, the CT imaging apparatus comprises: an X-ray source; a detector for detecting passing of the object; a digital image processing unit; and a CT trigger module for data acquisition, wherein during the object passes the CT imaging apparatus, the CT trigger module triggers the CT imaging apparatus to perform data acquisition every time the object passes the CT imaging apparatus a predetermined distance B along the convey path.

BRIEF DESCRIPTION OF DRAWINGS

The attached drawings of the present invention will be described below for more complete understanding of the present invention and showing of practicing the present invention, wherein

FIG. 2 schematically shows a DR image of an object obtained by a DR imaging apparatus which is not operated in a distance triggered mode, wherein FIG. 2a is a sectional view of the object, and FIG. 2b is the DR image;

FIG. 3 schematically shows a DR image of an object obtained by a DR imaging apparatus which is operated in a distance triggered mode, wherein FIG. 3a is a sectional view of the object, and FIG. 3b is the DR image.

DETAILED DESCRIPTION OF EMBODIMENTS

Exemplary embodiments of the present disclosure will be described hereinafter in detail with reference to the attached drawings. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

Figure 2:
Figure 2:
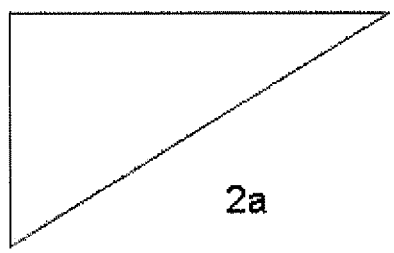
Figure 2:
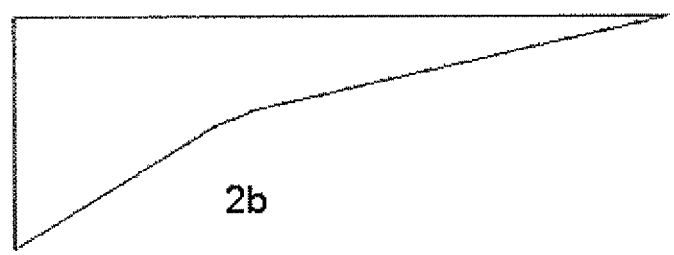

As mentioned above, if one object or article to be inspected is scanned at different moving speeds in a time triggered mode (at equal time interval), the formed image is distorted, as shown in FIG. 2. Therefore, in the time triggered mode in the prior art, there is still a technical problem of image distortion in the case that the object is scanned by both the DR imaging apparatus and the CT imaging apparatus at the same time.

Figure 1:
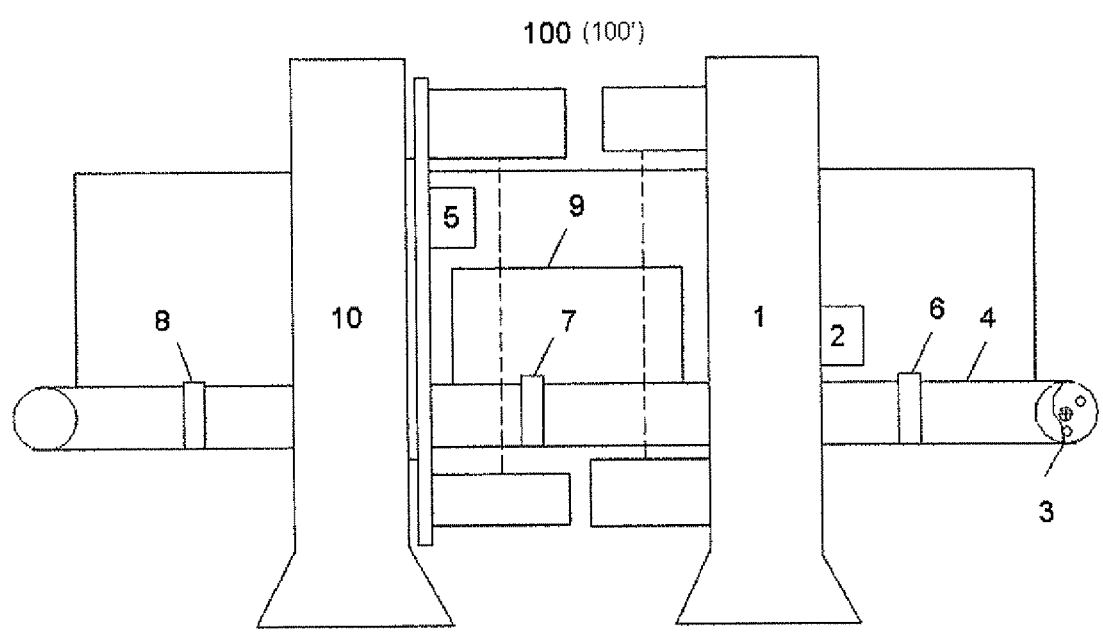
FIG. 1 is a schematic view of an inspection system of the present invention.

In view of the above technical problem, an inspection system 100 is provided. The inspection system 100 according to the present invention may be an Explosive Detection System or other systems which can identify or detect a passing object in suspicion. As shown in FIG. 1, the detection system 100 is used for inspecting an object 9 being conveyed along a convey path 4, the detection system 100 comprises a DR imaging apparatus 1 and a CT imaging apparatus 10 which is provided at the downstream or upstream of the DR imaging apparatus along the convey path 4, wherein an average speed at which the object 9 passes the DR imaging apparatus 1 is higher than an average speed at which the object 9 passes the CT imaging apparatus 10. Though FIG. 1 shows that the DR imaging apparatus 1 is at the upstream of the CT imaging apparatus 10, the DR imaging apparatus 1 may be at the downstream of the CT imaging apparatus 10.

The DR imaging apparatus 1 may comprise a DR trigger module 2 for data acquisition, and during the object 9 passes the DR imaging apparatus 1, the DR trigger module 2 triggers the DR imaging apparatus 1 to perform data acquisition every time the object 9 passes the DR imaging apparatus 1 a predetermined distance A along the convey path 4. The DR trigger module 2 may comprise a rotary encoder 3 provided on the convey path 4, the rotary encoder 3 outputs a trigger signal to trigger the DR imaging apparatus to perform data acquisition every time it rotates one predetermined angle, wherein every time the rotary encoder rotates one predetermined angle, the object passes the predetermined distance A along the convey path.

Alternatively, the DR trigger module 2 comprises a plurality of position marks (not shown) arranged apart at the predetermined distance A along the convey path 4, and a mark detector (not shown) for detecting the passing of the position marks, wherein every time the mark detector detects the passing of one of the position marks, the mark detector outputs a trigger signal to trigger the DR imaging apparatus to perform data acquisition.

Alternatively, the DR trigger module 2 may operate in a time triggered mode so that the DR trigger module 2 triggers the DR imaging apparatus 1 to perform data acquisition every time the object passes the DR imaging apparatus 1 the predetermined distance A along the convey path 4. That is, once a predetermined period of time, within which the convey path moves the predetermined distance A, lapses, the DR trigger module 2 triggers the DR imaging apparatus 1 to perform data acquisition.

The CT imaging apparatus 10 may comprise a CT trigger module 5 for data acquisition which functions similarly to the DR trigger module 2, and during the object 9 passes the CT imaging apparatus 10, the CT trigger module 5 triggers the CT imaging apparatus 10 to perform data acquisition every time the object 9 passes the CT imaging apparatus 10 a predetermined distance B along the convey path 4. The predetermined distance B is equal or unequal to the predetermined distance A.

Similarly, the CT trigger module 5 may comprise a rotary encoder (not shown) provided on the convey path, the rotary encoder outputs a trigger signal to trigger the CT imaging apparatus 10 to perform data acquisition every time it rotates one predetermined angle, wherein every time the rotary encoder rotates one angle, the object 9 passes the predetermined distance B along the convey path 4.

In a similar way, the CT trigger module 5 may comprise a plurality of position marks (not shown) arranged apart at the predetermined distance B along the convey path 4, and a mark detector for detecting the passing of the position marks, wherein every time the mark detector detects the passing of one of the position marks, the mark detector outputs a trigger signal to trigger the CT imaging apparatus 10 to perform data acquisition.

Also, the CT trigger module 5 operates in a time triggered mode so that the CT trigger module 5 triggers the CT imaging apparatus 10 to perform data acquisition every time the object 9 passes the CT imaging apparatus 10 the predetermined distance B along the convey path 4. That is, once a predetermined period of time, within which the convey path 4 moves the predetermined distance B, lapses, the CT trigger module 5 triggers the CT imaging apparatus 10 to perform data acquisition.

It should be noted that, in an alternative embodiment, the CT imaging apparatus 10 and the DR imaging apparatus 1 may share one rotary encoder or share one mark detector.

As shown in FIG. 1, the inspection system 100 further comprises a detector C for detecting passing of a front end of the object 9, the detector C is provided at a position in front of the downstream imaging apparatus (in FIG. 1, it is the CT imaging apparatus 10) by a predetermined distance C, and when the detector C detects the passing of the front end of the object 9, the downstream imaging apparatus begins to perform data acquisition.

In addition, the detection system 100 may further comprise a detector D for detecting passing of a front end of the object 9, the detector D is provided at a position in front of the downstream imaging apparatus by a predetermined distance D, wherein after the detector D detects the passing, the convey path decelerates from a first speed to a second speed within the predetermined distance D, and then the downstream imaging apparatus begins to perform data acquisition, or the convey path accelerates from the second speed to the first speed within the predetermined distance D, and then the downstream imaging apparatus begins to perform data acquisition.

In FIG. 1, the detector C or the detector D is indicated by the reference numeral 7.

The inspection system 100 may further comprise an upstream detector 6 for detecting passing of the front end of the object 9, the upstream detector 6 is provided at a position in front of the upstream imaging apparatus, wherein when the upstream detector detects the passing of the front end of the object 9, the upstream imaging apparatus begins to perform data acquisition. Moreover, the detection system 100 may comprise a downstream detector 8 for detecting passing of a rear end of the object, the downstream detector is provided at a position behind the downstream imaging apparatus, wherein when a predetermined time (as necessary at site) lapses from the detection of the passing of the rear end and the upstream detector 6 does not detect the passing of the front end of the object 9, the detection system stops operating or enters a standby state.

Please be noted that in the present application, the passing of the front end of the object 9 means that the front edge of the front end of the object 9 passes the upstream detector 6 or the detector 7 (the detector C and the detector D); the passing of the rear end of the object 9 means that the rear edge of the rear end of the object 9 passes the downstream detector 8. Moreover, in the present invention, the upstream detector 6, the detector 7 and the downstream detector 8 may be photoelectric switches. In addition, according to an exemplary embodiment, the predetermined distance A or B may be several micrometers or several centimeters according to the requested inspection precision, and the convey path 4 may be a ring-shape convey belt.

Next, another embodiment of the detection system according to the present invention will be described.

An detection system 100' comprises: a convey path 4 for an object 9; and a DR imaging apparatus 1 arranged along the convey path 4, wherein the DR imaging apparatus 1 comprises a DR trigger module 2 for data acquisition, and during the object passes the DR imaging apparatus 1, the DR trigger module 2 triggers the DR imaging apparatus 1 to perform data acquisition every time the object 9 passes the DR imaging apparatus 1 a predetermined distance A along the convey path 4.

The detection system 100' may further comprise a CT imaging apparatus 10 which is provided at the downstream or upstream of the DR imaging apparatus 1 along the convey path 4. Further, an average speed at which the object 9 passes the DR imaging apparatus 1 is higher than an average speed at which the object 9 passes the CT imaging apparatus 10.

The CT imaging apparatus 10 may comprise a CT trigger module 5 for data acquisition, and during the object 9 passes the CT imaging apparatus 10, the CT trigger module 5 triggers the CT imaging apparatus 10 to perform data acquisition every time the object 9 passes the CT imaging apparatus 10 a predetermined distance B along the convey path, wherein the predetermined distance B is equal or unequal to the predetermined distance A; the detection system 100' may further comprise a detector C for detecting passing of a front end of the object 9, the detector C is provided at a position in front of the downstream imaging apparatus by a predetermined distance C, and when the detector C detects the passing, the downstream imaging apparatus begins to perform data acquisition.

Alternatively, the detection system 100' further comprises a detector D for detecting passing of a front end of the object 9, the detector D is provided at a position in front of the downstream imaging apparatus by a predetermined distance D, wherein after the detector D detects the passing, the convey path decelerates from a first speed to a second speed within the predetermined distance D, and then the downstream imaging apparatus begins to perform data acquisition, or the convey path accelerates from the second speed to the first speed within the predetermined distance D, and then the downstream imaging apparatus begins to perform data acquisition.

In FIG. 1, the detector C or the detector D is indicated by the reference numeral 7.

The detection system 100' may further comprise a downstream detector 8 for detecting passing of a rear end of the object 9, the downstream detector 8 is provided at a position behind the downstream imaging apparatus, wherein when a predetermined time lapses from the detection of the passing of the rear end and the upstream detector 6 does not detect the passing of the front end of the object, the detection system stops operating or enters a standby state.

Moreover, the present invention relates to a DR imaging apparatus 1 for forming an image of an object 9 by scanning the object 9, the object being conveyed along a convey path 4, the DR imaging apparatus 1 comprises: an X-ray source (not shown); a detector for detecting passing of the object; a digital image processing unit; and a DR trigger module 2 for data acquisition, wherein during the object 9 passes the DR imaging apparatus 1, the DR trigger module 2 triggers the DR imaging apparatus 1 to perform data acquisition every time the object 9 passes the DR imaging apparatus 1 a predetermined distance A along the convey path 4. In other words, the DR trigger module 2 triggers in a distance triggered fashion the DR imaging apparatus 1 to perform data acquisition, once the object 9 on the convey path 4 passes the predetermined distance A (no matter what manner), the DR trigger module 2 will be triggered so as to control the DR imaging apparatus 1 to emit X-Ray beams and perform data acquisition. The DR imaging apparatus according to the present invention is controlled in a distance triggered fashion so that the performance of the DR imaging apparatus will not be adversely affected by the speed, high or low, uniform or non-uniform, of the object 9 relative to the DR imaging apparatus.

For the purpose of using the distance triggered mode, the DR trigger module 2 comprises a rotary encoder 3 provided on the convey path 4, the rotary encoder 3 outputs a trigger signal to trigger the DR imaging apparatus 1 to perform data acquisition every time it rotates one predetermined angle, wherein every time the rotary encoder 3 rotates the predetermined angle, the object 9 passes the predetermined distance A along the convey path 4. Regardless of the rotating speed of the rotary encoder 3, once it rotates one predetermined angle, it will send a trigger signal. The rotary encoder 3 here may comprise a gear wheel at one end thereof, the teeth of the gear wheel contact the convey path 4 by rolling, so that once the convey path 4 moves forwards the predetermined distance A, the gear wheel rotates one predetermined angle. The rotary encoder 3 may be any other form as long as it rotates one predetermined angle when the convey path 4 moves forward the predetermined distance A. Alternatively, the DR trigger module 2 may comprise a plurality of position marks (not shown) arranged apart at the predetermined distance A along the convey path 4, and a mark detector (not shown) for detecting the passing of the position marks, wherein every time the mark detector detects the passing of one of the position marks, the mark detector outputs a trigger signal to trigger the DR imaging apparatus to perform data acquisition.

The CT imaging apparatus 10 may be operated in the above distance triggered mode. Therefore, the present invention also relates to a CT imaging apparatus for forming an image of an object 9 by scanning the object, the object being conveyed along a convey path, the CT imaging apparatus 10 comprising: an X-ray source; a detector for detecting passing of the object; a digital image processing unit; and a CT trigger module 5 for data acquisition, wherein during the object passes the CT imaging apparatus, the CT trigger module 5 triggers the CT imaging apparatus 10 to perform data acquisition every time the object 9 passes the CT imaging apparatus a predetermined distance B along the convey path 4.

Next, the operation process of the detection system 100 according to the present invention will be described with reference to FIG. 1 by way of example.

As shown in FIG. 1, the DR imaging apparatus 1 is positioned near the inlet of the detection system 100, while the CT imaging apparatus 10 is located near the outlet of the detection system 100. The operation process of the detection system 100 is as follows:

(1) The object 9 on the convey path 4 enters the detection system 100 through the inlet at a higher speed.

(2) After the front end of the object 9 passes the upstream detector 6 located in front of the DR imaging apparatus 1, the DR imaging apparatus 1 emits beams, and the DR trigger module 2 begins to operate.

(3) The DR trigger module 2 operates in a distance triggered detection. The rotary encoder 3 rotates with the movement of the convey path 4 by, for example, a rolling contact with the convey path 4, and every time the convey path 4 moves one distance, the rotary encoder 3 rotates one angle, and further the rotary encoder 3 sends a trigger signal to the DR imaging apparatus if it rotates one predetermined angle. Thus, the DR imaging apparatus 1 performs one data acquisition every one certain distance (for example, the convey path 4 moves a certain distance), the acquired data are processed later to form DR images.

(4) When the object 9 is in front of the CT imaging apparatus 10 by a predetermined distance (for example, the object 9 is at a position away from the CT beam plane by a distance larger than two times of the CT slice thickness), or when the front end of the object passes the detector 7 (the detector D) provided at the upstream of the CT imaging apparatus, the convey path 4 is controlled to decelerate so that the convey path 4 slows down to a lower speed within the predetermined distance (for example, at a position away from the CT beam plane by a distance of the CT slice thickness) and then moves uniformly at a first speed, at the same time, the CT imaging apparatus 10 is triggered to emit beams to perform data acquisition.

(5) The CT trigger module 5 controls, in a time triggered manner, the CT imaging apparatus 10 to emit beams so that the data acquisition is performed every certain time interval, the acquired data are processed to form CT images which can be analyzed automatically to identify materials of the object. The perspective view and stratigrams of the object are provided, and an alarm is given if necessary. However, the CT trigger module 5 may control the CT imaging apparatus 10 to emit beams in a distance triggered manner, as mentioned above.

(6) If the length of the object 9 is longer than the distance between the DR beam plane and the CT beam plane, there is the case that the object 9 is scanned by both the CT imaging apparatus 10 and the DR imaging apparatus 1 at the same time, however, since the DR imaging apparatus is triggered with distance to perform data acquisition, the frequency of image capturing of the DR imaging apparatus is independent of the speed of the convey path 4, thus the quality of the image captured is ensured.

(7) When a predetermined time (as necessary at site) lapses from the detection of the passing of the rear end of the object 9 by the downstream detector 8, and the upstream detector 6 does not detect the passing of the front end of the object 9, the inspection system 100 stops operating or enters a standby state.

Figure 3:
Figure 3:
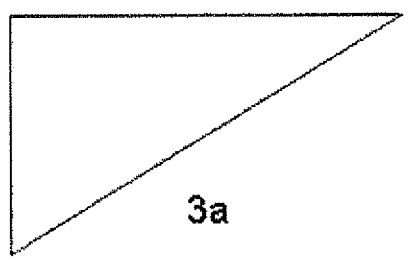
Figure 3:
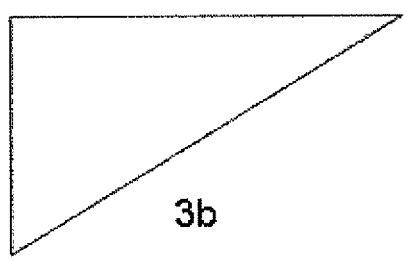

Because the DR imaging apparatus is triggered by the DR trigger module in a distance triggered mode, the formed images having stable quality is obtained though the convey path moves at different speeds. During the data acquisition, the DR imaging apparatus is triggered in the distance triggered mode, thus, acquiring data at different speeds is realized. Therefore, the object on the convey path of the detection system may be scanned by the DR imaging apparatus at a higher speed and then be scanned by both the DR imaging apparatus and the CT imaging apparatus at the same time at a lower speed, and then be scanned by the CT imaging apparatus at the lower speed. If the CT imaging apparatus is at the upstream of the DR imaging apparatus, the object on the convey path of the inspection system may be scanned by the CT imaging apparatus at a lower speed and then be scanned at the lower speed by both the DR imaging apparatus and the CT imaging apparatus at the same time, and then be scanned by the DR imaging apparatus at a higher speed. Obviously, the detection system and the detection method according to the present invention increase the speed at which the object passes the inspection system while the formed images having good quality is ensured (as shown in FIG. 3, the DR image obtained according to the present invention is not distorted).

Although a few embodiments have been shown and described, it would be appreciated by those of ordinary skill in the art that changes and variants may be made in these embodiments without departing from the principles and spirit of the invention, the scope of which is defined in the claimed and their equivalents.

The invention claimed is:

1. A detection system for detecting an object being conveyed along a convey path, the detection system comprises a DR imaging apparatus and a CT imaging apparatus which is provided at the downstream or upstream of the DR imaging apparatus along the convey path, wherein
   an average speed at which the object passes the DR imaging apparatus is higher than an average speed at which the object passes the CT imaging apparatus,
   the DR imaging apparatus comprises a DR trigger module for data acquisition, and
   during the object passes the DR imaging apparatus, the DR trigger module triggers the DR imaging apparatus to perform data acquisition every time the object passes a predetermined distance A along the convey path.

2. The detection system according to claim 1, wherein
   the DR trigger module comprises a rotary encoder provided on the convey path, the rotary encoder outputs a trigger signal to trigger the DR imaging apparatus to perform data acquisition every time it rotates one predetermined angle, wherein every time the rotary encoder rotates the predetermined angle, the object passes the predetermined distance A along the convey path.

3. The detection system according to claim 1, wherein
The DR trigger module comprises a plurality of position marks arranged apart at the predetermined distance A along the convey path, and a mark detector for detecting the passing of the position marks, wherein every time the mark detector detects the passing of one of the position marks, the mark detector outputs a trigger signal to trigger the DR imaging apparatus to perform data acquisition.

4. The detection system according to claim 1, wherein
the DR trigger module operates in a time triggered mode so that the DR trigger module triggers the DR imaging apparatus to perform data acquisition every time the object passes the predetermined distance A along the convey path.

5. The detection system according to claim 1, further comprises a detector D for detecting passing of a front end of the object, the detector D is provided at a position in front of the downstream imaging apparatus by a predetermined distance D, wherein after the detector D detects the passing, the convey path decelerates from a first speed to a second speed within the predetermined distance D, and then the downstream imaging apparatus begins to perform data acquisition, or the convey path accelerates from the second speed to the first speed within the predetermined distance D, and then the downstream imaging apparatus begins to perform data acquisition.

6. The detection system according to claim 1, further comprises an upstream detector for detecting passing of a front end of the object, the upstream detector is provided at a position in front of the upstream imaging apparatus, wherein when the upstream detector detects the passing, the upstream imaging apparatus begins to perform data acquisition.

7. The detection system according to claim 6, further comprises a downstream detector for detecting passing of a rear end of the object, the downstream detector is provided at a position behind the downstream imaging apparatus, wherein when a predetermined time lapses from the detection of the passing of the rear end and the upstream detector does not detect the passing of the front end of the object, the inspection system stops operating or enters a standby state.

8. A detection system for detecting an object being conveyed along a convey path, the detection system comprises a DR imaging apparatus and a CT imaging apparatus which is provided at the downstream or upstream of the DR imaging apparatus along the convey path, wherein
an average speed at which the object passes the DR imaging apparatus is higher than an average speed at which the object passes the CT imaging apparatus,
the CT imaging apparatus comprises a CT trigger module for data acquisition, and
during the object passes the CT imaging apparatus, the CT trigger module triggers the CT imaging apparatus to perform data acquisition every time the object passes a predetermined distance B along the convey path.

9. The detection system according to claim 8, wherein
the CT trigger module comprises a rotary encoder provided on the convey path, the rotary encoder outputs a trigger signal to trigger the CT imaging apparatus to perform data acquisition every time it rotates one angle, wherein every time the rotary encoder rotates one predetermined angle, the object passes the predetermined distance B along the convey path.

10. The detection system according to claim 8, wherein
the CT trigger module comprises a plurality of position marks arranged apart at the predetermined distance B along the convey path, and a mark detector for detecting the passing of the position marks, wherein every time the mark detector detects the passing of one of the position marks, the mark detector outputs a trigger signal to trigger the CT imaging apparatus to perform data acquisition.

11. The detection system according to claim 8, wherein
the CT trigger module operates in a time triggered mode so that the CT trigger module triggers the CT imaging apparatus to perform data acquisition every time the object passes the predetermined distance B along the convey path.

12. The detection system according to claim 8, further comprises a detector C for detecting passing of a front end of the object, the detector C is provided at a position in front of the downstream imaging apparatus by a predetermined distance C, and when the detector C detects the passing, the downstream imaging apparatus begins to perform data acquisition.

13. A detection system comprising:
a convey path for conveying an object to be inspected; and
a DR imaging apparatus arranged along the convey path,
wherein the DR imaging apparatus comprises a DR trigger module for data acquisition, and during the object passes the DR imaging apparatus, the DR trigger module triggers the DR imaging apparatus to perform data acquisition every time the object passes a predetermined distance A along the convey path, wherein the detection system further comprises a CT imaging apparatus which is provided at the downstream or upstream of the DR imaging apparatus along the convey path; and an average speed at which the object passes the DR imaging apparatus is higher than an average speed at which the object passes the CT imaging apparatus.

14. The detection system according to claim 13, wherein
the CT imaging apparatus comprises a CT trigger module for data acquisition, and during the object passes the CT imaging apparatus, the CT trigger module triggers the CT imaging apparatus to perform data acquisition every time the object passes a predetermined distance B along the convey path,
the detection system further comprises a detector C for detecting passing of a front end of the object, the detector C is provided at a position in front of the downstream imaging apparatus by a predetermined distance C, and when the detector C detects the passing, the downstream imaging apparatus begins to perform data acquisition.

15. The detection system according to claim 13, further comprises a detector D for detecting passing of a front end of the object, the detector D is provided at a position in front of the downstream imaging apparatus by a predetermined distance D, wherein after the detector D detects the passing, the convey path decelerates from a first speed to a second speed within the predetermined distance D, and then the downstream imaging apparatus begins to perform data acquisition, or the convey path accelerates from the second speed to the first speed within the predetermined distance D, and then the downstream imaging apparatus begins to perform data acquisition.

16. The detection system according to claim 13, further comprises an upstream detector for detecting passing of a front end of the object, the upstream detector is provided at a position in front of the upstream imaging apparatus, wherein when the upstream detector detects the passing, the upstream imaging apparatus begins to perform data acquisition.

17. The detection system according to claim 16, further comprises a downstream detector for detecting passing of a rear end of the object, the downstream detector is provided at a position behind the downstream imaging apparatus, wherein when a predetermined time lapses from the detection of the passing of the rear end and the upstream detector does not detect the passing of the front end of the object, the detection system stops operating or enters a standby state.

18. A DR imaging apparatus for forming an image of an object to be detected by scanning the object, the object being conveyed along a convey path, the DR imaging apparatus comprising:
　　an X-ray source;
　　a detector for detecting passing of the object;
　　a digital image processing unit; and
　　a DR trigger module for data acquisition,
　　wherein during the object passes the DR imaging apparatus, the DR trigger module triggers the DR imaging apparatus to perform data acquisition every time the object a predetermined distance A along the convey path, wherein the DR trigger module comprises a plurality of position marks arranged apart at the predetermined distance A along the convey path, and a mark detector for detecting the passing of the position marks, wherein every time the mark detector detects the passing of one of the position marks, the mark detector outputs a trigger signal to trigger the DR imaging apparatus to perform data acquisition.

19. A CT imaging apparatus for forming an image of an object to be detected by scanning the object, the object being conveyed along a convey path, the CT imaging apparatus comprising:
　　an X-ray source;
　　a detector for detecting passing of the object;
　　a digital image processing unit; and
　　a CT trigger module for data acquisition,
　　wherein during the object passes the CT imaging apparatus, the CT trigger module triggers the CT imaging apparatus to perform data acquisition every time the object passes a predetermined distance B along the convey path.

* * * * *